(12) United States Patent
Lee et al.

(10) Patent No.: US 11,499,174 B2
(45) Date of Patent: Nov. 15, 2022

(54) METHOD OF CONTINUOUSLY PRODUCING GLUTATHIONE USING PHOTOSYNTHETIC MEMBRANE VESICLES

(71) Applicant: SOGANG UNIVERSITY RESEARCH FOUNDATION, Seoul (KR)

(72) Inventors: Jeong Kug Lee, Seoul (KR); Hyeon Jun Kim, Seoul (KR); Eun Kyoung Oh, Seoul (KR)

(73) Assignee: SOGANG UNIVERSITY RESEARCH FOUNDATION, Seoul (KR)

( * ) Notice: Subject to any disclaimer, the term of this patent is extended or adjusted under 35 U.S.C. 154(b) by 214 days.

(21) Appl. No.: 16/442,849

(22) Filed: Jun. 17, 2019

(65) Prior Publication Data
US 2019/0309340 A1    Oct. 10, 2019

Related U.S. Application Data

(62) Division of application No. 15/543,909, filed as application No. PCT/KR2016/000433 on Jan. 15, 2016, now abandoned.

(30) Foreign Application Priority Data

Jan. 16, 2015    (KR) .................. 10-2015-0008174

(51) Int. Cl.
| C12P 21/02 | (2006.01) |
| C12N 9/00 | (2006.01) |
| C07K 5/093 | (2006.01) |

(52) U.S. Cl.
CPC ............ *C12P 21/02* (2013.01); *C07K 5/0819* (2013.01); *C12N 9/00* (2013.01); *C12N 9/93* (2013.01); *C12Y 603/02002* (2013.01); *C12Y 603/02003* (2013.01)

(58) Field of Classification Search
CPC ......... C12P 21/02; C07K 5/0819; C12N 9/00; C12N 9/93; C12Y 603/02002; C12Y 603/02003
See application file for complete search history.

(56) References Cited

U.S. PATENT DOCUMENTS

2008/0194701 A1    8/2008 Griffith et al.

FOREIGN PATENT DOCUMENTS

| CN | 102071171 A | 5/2011 |
| CN | 102220400 A | 10/2011 |
| CN | 103627691 A | 3/2014 |
| JP | 56-117797 A | 9/1981 |
| JP | 01-228473 A | 12/1989 |
| JP | 2012-513213 A | 6/2012 |
| WO | 2010074760 A1 | 7/2010 |

OTHER PUBLICATIONS

KEGG Enzyme; 6.3.2.2, 2 pages of PDF, retrieved from KEGG enzyme database genome.jp/entry/6.3.2.2, on Aug. 3, 2021.*
Hara et al., Biotechnol Lett, 2011, vol. 33, p. 1133-1138.*
Sener et al., Biophysical Journal, 2010, vol. 99, No. 1, p. 67-75.*
KEGG Enzyme; 6.3.2.3, 2 pages of PDF, retrieved from KEGG enzyme database genome.jp/entry/6.3.2.3, on Aug. 3, 2021.*
Creissen et al., "Elevated Glutathione Biosynthetic Capacity in the Chloroplasts of Transgenic Tobacco Plants Paradoxically Causes Increased Oxidative Stress," Jul. 1999, pp. 1277-1291, The Plant Cell, vol. 11.
Sawa et al., "Photosynthetic Glutathione Production Using Intact yanobacterial Cells," 1986, pp. 1361-1363, Agricultural and Biological Chemistry, vol. 50, No. 5.
Dani et al., "Isolation and characterization of a thylakoid membrane module showing partial light and dark reactions," 2005, pp. 43-52, Science Direct, Biochimica et Biophysica Acta 1669.
Janowiak et al., "Glutathione Synthesis in *Streptococcus agalactiae*," 2005, pp. 11829-11839, The Journal of Biological Chemistry, vol. 280, No. 2.
Vergauwen et al., "Characterization of the Bifunctional-Glutamate-cysteine Ligase/Glutathione Synthetase (GshF) of Pasteurella multocida," 2005, pp. 4380-4394, The Journal of Biological Chemistry, vol. 281, No. 7.
Li et al., "Glutathione: a review on biotechnological production," 2004, pp. 233-244, Appl. Microbiology Biotechnology, vol. 66.
Harington et al., "CXCIV. Synthesis of Glutathione." 1935, pp. 1602-1611, Biochemical Journal, vol. 29.
Wu et al., "Recent Advances in Nutritional Sciences: Glutathione Metabolism and its Implications for Health," 2004, pp. 489-492, The Journal of Nutrition.
Okubo et al., "Characterization of Phototrophic Purple Nonsulfur Bacteria Forming Colored Microbial Mats in a Swine Wastewater Ditch," 2006, pp. 6225-6233, Applied and Environmental Microbiology, vol. 72, No. 9.
Patent Cooperation Treaty, International Search Report for PCT/KR2016000433, dated May 30, 2016, 2 pages.

(Continued)

*Primary Examiner* — Kade Ariani
(74) *Attorney, Agent, or Firm* — Heslin Rothenberg Farley & Mesiti P.C.

(57) ABSTRACT

The present invention relates to a method of producing glutathione, wherein photosynthetic membrane vesicles and enzymes catalyzing glutathione synthesis are combined and glutamate, cysteine and glycine are used as reaction substrates. As enzymes catalyzing glutathione synthesis, γ-glutamylcysteine synthetase and glutathione synthetase may be used together, or bifunctional glutathione synthetase may be used alone. According to the conventional methods, there is a problem in that expensive adenosine triphosphate should be continuously supplied when glutathione is produced. However, according to the present invention, since photosynthetic membrane vesicles are used as a source to regenerate adenosine triphosphate, it is possible to continuously produce glutathione without additionally adding adenosine triphosphate, thereby reducing production costs of glutathione.

2 Claims, 9 Drawing Sheets
Specification includes a Sequence Listing.

(56) References Cited

OTHER PUBLICATIONS

Hara et al., ATP Photosynthetic vesicles for light-driven Bioprocesses, Biotechnol Letter, Feb. 2, 2011, vol. 33, p. 1133 Only.
Sener et al., Photosynthetic Vesicle Architecture and Constraints on Efficient Energy Harvesting, Biophysical Journal, vol. 99, Jul. 2010, p. 67 Only.
Scheuring et al., The architecture of Rhodobacter sphaeroides chromatophores, Biochimica et Biophysica Acta, vol. 1837, Mar. 11, 2014, pp. 1263-1270.
Sener et al., Atomic-level structural and functional model of a bacterial photosynthetic membrance vesicle, Proceedings of The National Academy of Sciences of The United States of America, Oct. 2, 2007, vol. 104, No. 40, pp. 15723-15728.
Supplementary European Search Report for corresponding European application EP 16 73 7582, dated Jun. 15, 2018.
Office Action issued in corresponding Japanese Patent Application No. 2017-537981, dated May 31, 2018.
Nevo et al., The EMBO Journal (2007) 26, pp. 1467-1473.
Patent Cooperation Treaty, Written Opinion of the International Search Authority for PCT/KR2016000433, dated May 30, 2016, 11 Pages.
Office Action, with English-language translation, issued in connection with Chinese application No. 2016800151189 dated Apr. 3, 2020.

* cited by examiner

METHOD OF CONTINUOUSLY PRODUCING GLUTATHIONE USING PHOTOSYNTHETIC MEMBRANE VESICLES

CROSS REFERENCE TO RELATED APPLICATIONS

This application is a divisional of U.S. application Ser. No. 15/543,909, filed Jul. 14, 2017, as a national stage filing under 36 U.S.C. section 371 of International Application No. PCT/KR2016/000433, filed on January 15, 2016, published in Korean on Jul. 21, 2016, as WO2016/114618 A1 and claims priority to Korean Application No. 10-2015-0008174, filed on Jan. 15, 2015, the entire disclosures of which applications being hereby incorporated herein by reference.

SEQUENCE LISTING

The instant application contains an electronic sequence listing. The content of the electronic sequence listing (H2458969.txt; Size: 1,753 bytes; and Date of Creation: Sep. 12, 2022) is herein incorporated by reference in its entirety.

TECHNICAL FIELD

The present invention relates to a method of continuously producing glutathione using photosynthetic membrane vesicles.

BACKGROUND ART

Glutathione (GSH) is a tripeptide composed of L-glutamate, L-cysteine, and glycine and is synthesized in most eukaryotes and some prokaryotes. Glutathione is biosynthesized by two step enzymatic reactions catalyzed by γ-glutamylcysteine synthetase (GSH-I, EC 6.3.2.2) and glutathione synthetase (GSH-II, EC 6.3.2.3) using L-glutamate, L-cysteine, and glycine as starting materials. Recent studies have revealed a novel biosynthetic pathway mediated by one enzyme in addition to the previously known glutathione synthesis pathway mediated by the two enzymes mentioned above, and it has been found that an enzyme catalyzing the novel biosynthetic pathway is bifunctional glutathione synthetase (bifunctional γ-glutamylcysteine synthetase/glutathione synthetase, GshF) (see Janowiak and Griffith. 2005. J. Biol. Chem. 280: 11829-11839, Vergauwen et al. 2006. J. Biol. Chem. 281: 4380-4394).

Glutathione contains a thiol group having strong reducing power, and it acts in vivo in concert with glutathione peroxidase (GSH peroxidase), glutathione reductase (GSH reductase), and glutathione S-transferase (GSH S-transferase) to perform an antioxidant function. It may be involved in immune stimulation and detoxification of xenobiotics (see Pastore et al. 2003. Clinica Chimica Acta 333: 19-39). In general, it is known that glutathione synthesis genes are essential for survival, and organisms deficient in these genes are less resistant to oxidative stress and various harmful substances. In addition, there is a report that various human diseases are associated with a decrease in glutathione concentration in body (Wu et al. 2004. J. Nutr. 134: 489-492). Accordingly, based on the antioxidant activity of glutathione, glutathione is widely used as an additive in foods, medicines and cosmetics for the purpose of preventing aging and promoting health.

To date, known methods of producing glutathione include organic synthesis methods, enzymatic methods, and fermentative methods. The organic synthesis method refers to a method of chemically synthesizing glutathione, and was developed in 1935 and commercialized in 1950 (Harington and Mead. 1935. Biochem. J. 29: 1602-1611, Li et al. 2004. Appl. Microbiol. Biotechnol. 66: 233-242). Glutathione synthesized by the organic synthesis method is optically inactive (racemic). However, since organisms selectively use only L-glutathione, an additional step of isolating L-glutathione is required to use glutathione synthesized by the organic synthesis method.

As soon as the biosynthetic pathway of glutathione was discovered in the 1950s, attempts to biologically produce glutathione began (Bloch. 1949. J. Biol. Chem. 179: 1245-1254). Among such methods, a method of producing glutathione by fermentation using *Escherichia coli* or yeast (*Saccharomyces cerevisiae* and *Candida* sp.) is currently the most commercially used method. In the fermentative method, glucose or molasses is used as a carbon source. Generally, *Escherichia coli* or yeast are cultured for 20 to 30 hours under fermentation conditions with the carbon source, and then glutathione is extracted. When the fermentation method is used to produce glutathione, various methods may be additionally performed to enhance glutathione production. For example, L-cysteine may be added to medium to enhance a glutathione production rate (Alfafara et al. 1992. Appl. Microbiol. Biotechol. 37: 141-146). In addition, efforts were made to increase glutathione production by overexpressing two genes (GSH-I, GSH-II) responsible for glutathione synthesis in fermentation strains, but no significant increase in glutathione production was observed.

Another way to biologically produce glutathione is to use enzymes. In commonly used biological methods, *Escherichia coli* or yeast is treated with a surfactant to increase the permeability to substrates, and then L-glutamate, L-cysteine, glycine and adenosine triphosphate are added to the surfactant-treated cells. After subsequent incubation, L-glutathione is produced in cells. As another example, there is a method of producing glutathione using purified γ-glutamylcysteine synthetase and glutathione synthetase, but the method is not widely used. The enzymatic methods are advantageous in that the reaction is selective and yield is higher than that of the fermentative methods. However, in the case of the methods, since the unit price of adenosine triphosphate required for the reaction is high, the enzymatic methods are difficult to commercialize. To overcome this cost problem, it is possible to supply adenosine triphosphate by using an enzyme that regenerates adenosine triphosphate or by using glycolysis that takes place in cells, but the cost problem cannot be completely solved by such methods. Therefore, when a system capable of continuously supplying adenosine triphosphate at low cost is provided, production of glutathione using enzymes is likely be commercialized.

The above described background art has been provided to aid in understanding of the present invention and should not be interpreted as conventional technology known to a person having ordinary skill in the art.

DISCLOSURE

Technical Problem

Glutathione is very useful as an additive in foods, medicines and cosmetics. When such glutathione is synthesized using enzymes, there is an advantage in that reaction process is simple, but there is a problem in that the unit cost of coenzymes used in the reaction process is expensive. Accordingly, the present inventors have studied a method of producing glutathione at a relatively low cost. As a result, vesicles present in the cell membranes of photosynthetic bacteria or algae were isolated, which contain apparatuses for performing photosynthetic light reaction. When enzymes that catalyze glutathione synthesis were added to the vesicles and then irradiated with light, it was verified that glutathione was continuously synthesized without continued addition of adenosine triphosphate or the like having a very high unit cost, thereby completing the present invention.

Therefore, it is an objective of the present invention to provide a method of producing glutathione using photosynthetic membrane vesicles and γ-glutamylcysteine synthetase and glutathione synthetase.

It is another objective of the present invention to provide a method of producing glutathione using photosynthetic membrane vesicles and bifunctional glutathione synthetase.

It is still another objective of the present invention to provide a composition including photosynthetic membrane vesicles for producing glutathione.

It is yet another objective of the present invention to provide a system for continuously producing glutathione, the system including photosynthetic membrane vesicles as a means for supplying adenosine triphosphate.

It is yet another objective of the present invention to provide a method of continuously producing glutathione, the method including a step of adding substrates for producing glutathione to the system.

Other objects and advantages of the present invention will become more apparent from the following detailed description of the invention, claims and drawings.

Technical Solution

One aspect of the present invention provides a method of producing glutathione using photosynthetic membrane vesicles, γ-glutamylcysteine synthetase (GSH-I) and glutathione synthetase (GSH-II).

Another aspect of the present invention provides a method of producing glutathione using photosynthetic membrane vesicles and bifunctional glutathione synthetase (bifunctional γ-glutamylcysteine synthetase/glutathione synthetase, GshF).

The present inventors have studied a method of continuously producing glutathione as an additive in foods, medicines and cosmetics. As a result, vesicles present in the cell membranes of photosynthetic bacteria or algae were isolated (photosynthetic membrane vesicles). When enzymes that catalyze glutathione synthesis were added to reaction mixture containing the vesicles, and then it was irradiated with light, glutathione was continuously synthesized without addition of adenosine triphosphate having a very high unit cost.

As used herein, "photosynthetic membrane vesicles" may be isolated in the form of vesicle from photosynthetic bacteria or algae capable of performing photosynthesis using light energy, and refer to cell membrane-protein complexes capable of conducting a photosynthetic reaction upon irradiation with appropriate wavelengths of light.

Photosynthetic membranes forming the photosynthetic membrane vesicles may include chromatophore membranes (also known as intracytoplasmic membranes, ICMs) present in anoxygenic photosynthetic bacteria and thylakoid membranes (TMs) present in oxygenic photosynthetic bacteria or algae.

Chromatophore membrane vesicles are derived from chromatophore membranes, and refer to cell membrane-protein complexes containing reaction centers, light-harvesting complexes, adenosine triphosphate synthase (ATP synthase) and electron transfer chain proteins. In chromatophore membranes, adenosine triphosphate is generated from adenosine diphosphate and an inorganic phosphate by a proton motive force formed as a result of cyclic electron flow. In addition, reduced nicotinamide adenine dinucleotide (NADH) may be generated from oxidized nicotinamide adenine dinucleotide ($NAD^+$) through reverse electron flow mediated by complex I and complex II present in chromatophore membranes. The generated NADH may be converted into reduced nicotinamide adenine dinucleotide phosphate (NADPH) by pyridine nucleotide transhydrogenase.

Anoxygenic photosynthetic bacteria from which the chromatophore membrane vesicles can be isolated are preferably purple non-sulfur bacteria, more preferably purple non-sulfur bacteria selected from the group consisting of *Rhodobacter* sp., *Rhodospirillum* sp., *Rhodopseudomonas* sp., *Roseobacter* sp., *Bradyrhizobium* sp., and *Rubrivivax* sp., without being limited thereto.

Thylakoid membrane vesicles are derived from thylakoid membranes, and refer to cell membrane-protein complexes containing two types of photosynthetic systems (photosystem I/II), adenosine triphosphate synthase and electron transfer chain proteins. Electron transfer using water as an electron donor occurs in thylakoid membranes, resulting in generation of reduced nicotinamide adenine dinucleotide phosphate (NADPH) and formation of the proton motive force. The formed proton motive force is used to synthesize adenosine triphosphate from adenosine diphosphate and an inorganic phosphate by adenosine triphosphate synthase.

Oxygenic photosynthetic bacteria or algae from which the thylakoid membrane vesicles can be isolated are preferably cyanobacteria, more preferably cyanobacteria selected from the group consisting of *Synechocystis* sp., *Synechococcus* sp., *Nostoc* sp., *Anabaena* sp., *Gloeobacter* sp., and *Cyanobacterium* sp., without being limited thereto.

According to a preferred embodiment of the present invention, the method of the present invention includes a step of generating adenosine triphosphate (ATP) from adenosine diphosphate (ADP) and an inorganic phosphate by irradiating the photosynthetic membrane vesicles with light.

Figure 1A:
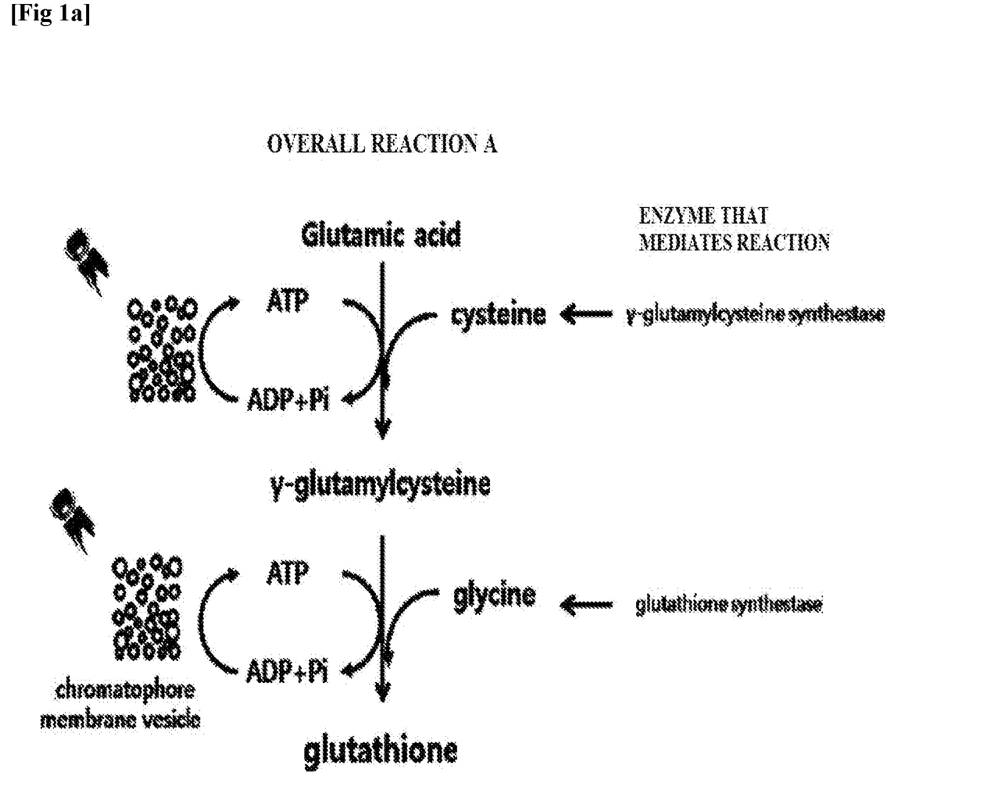
FIG. 1a illustrates a schematic diagram (overall reaction A) showing a method of synthesizing glutathione using chromatophore membrane vesicles, γ-glutamylcysteine synthetase and glutathione synthetase.
Figure 1B:
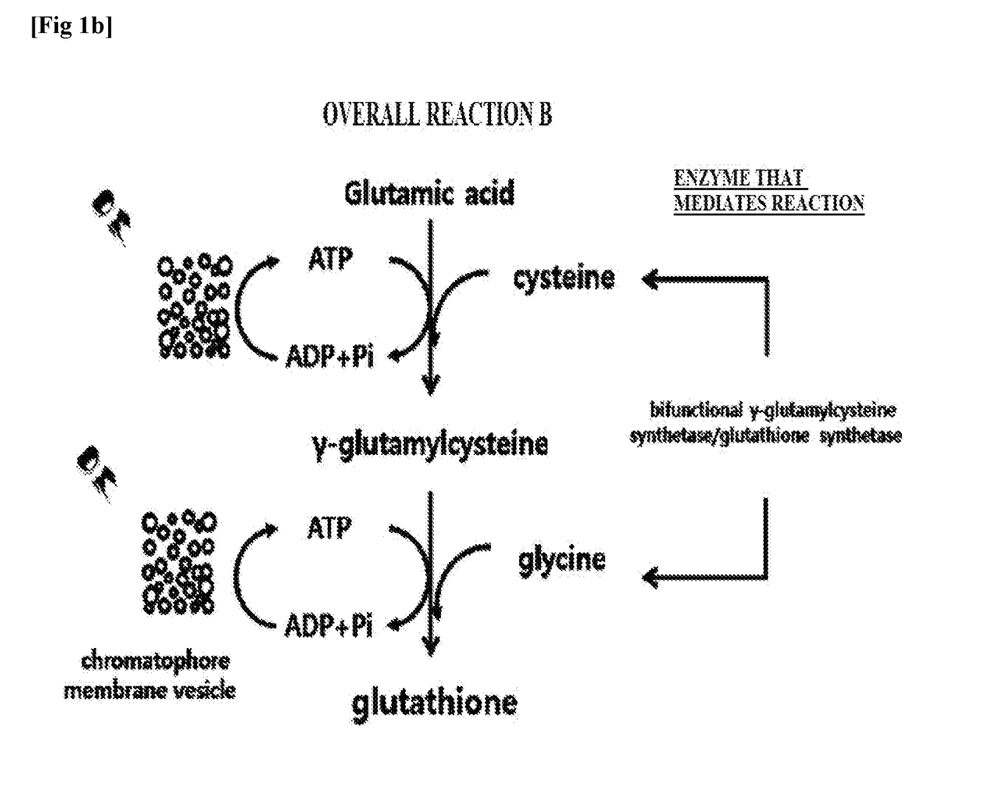
FIG. 1b illustrates a schematic diagram (overall reaction B) showing a method of synthesizing glutathione using chromatophore membrane vesicles and bifunctional glutathione synthetase.

In the present invention, photosynthetic membrane vesicles are used as a source of adenosine triphosphate and, in the process of producing glutathione, enzymes that catalyze glutathione synthesis consume adenosine triphosphate to form adenosine diphosphate and an inorganic phosphate (FIGS. 1a and 1b). The adenosine diphosphate and inorganic phosphate may be converted into adenosine triphosphate by a photoreaction carried out in photosynthetic membrane vesicles under photosynthesis conditions, and the adenosine triphosphate may be reused by enzymes involved in glutathione synthesis.

As used herein, the term "photosynthesis conditions" refer to conditions for inducing a photoreaction in photosynthetic membrane vesicles. For example, in the case of chromatophore membrane vesicles, a photoreaction is preferably carried out under conditions of a temperature range of 20 to 37° C., a luminous intensity range of 3 to 300 Watts/m$^2$ and irradiation with light having a wavelength of 350 to 1000 nm. An incandescent lamp may be used to meet this wavelength range. In addition, in the case of thylakoid membrane vesicles, a photoreaction is preferably carried out under conditions of a temperature range of 20 to 37° C., a light intensity range of 5 to 500 µEinstein/m²·s (µmole photons/m²·s) and irradiation with light having a wavelength of 400 to 700 nm. A fluorescent lamp may be used to meet this wavelength range.

Still another aspect of the present invention provides a method of producing glutathione including: a) a step of generating adenosine triphosphate (ATP) from adenosine diphosphate (ADP) and an inorganic phosphate by irradiating photosynthetic membrane vesicles; b) a step of synthesizing glutathione by enzymes that catalyze glutathione synthesis using ATP generated in step a), and forming ADP and an inorganic phosphate; and c) a step of reusing ADP and an inorganic phosphate generated in step b) to generate ATP by photosynthetic membrane vesicles.

As used herein, "enzymes that catalyze glutathione synthesis" refers to enzymes that consume adenosine triphosphate to form adenosine diphosphate and an inorganic phosphate, thereby catalyzing a reaction that produces glutathione, and preferably include one or more selected from the group consisting of γ-glutamylcysteine synthetase (GSH-I), glutathione synthetase (GSH-II) and bifunctional glutathione synthetase (bifunctional γ-glutamylcysteine synthetase/glutathione synthetase, GshF).

The enzymes that catalyze glutathione synthesis use substrates for producing glutathione, and preferably use glutamate, cysteine and glycine as substrates. Considering that organisms selectively produce L-glutathione and use the same, it is effective to use L-glutamate and L-cysteine for glutamate and cysteine.

According to a preferred embodiment of the present invention, among enzymes that catalyze glutathione synthesis, γ-glutamylcysteine synthetase catalyzes synthesis of γ-glutamylcysteine from glutamate and cysteine while converting adenosine triphosphate into adenosine diphosphate and an inorganic phosphate, and the glutathione synthetase catalyzes synthesis of glutathione from γ-glutamylcysteine and glycine while converting adenosine triphosphate into adenosine diphosphate and an inorganic phosphate.

That is, in the method, step b) may include a step of synthesizing γ-glutamylcysteine from glutamate and cysteine by γ-glutamylcysteine synthetase while converting adenosine triphosphate generated in step a) into adenosine diphosphate and an inorganic phosphate; and a step of synthesizing glutathione from the synthesized γ-glutamylcysteine and glycine by glutathione synthetase while converting adenosine triphosphate generated in step a) into adenosine diphosphate and an inorganic phosphate (see overall reaction A of FIG. 1a).

According to a preferred embodiment of the present invention, among the enzymes that catalyze glutathione synthesis, bifunctional glutathione synthetase is capable of both the reaction catalyzed by γ-glutamylcysteine synthetase and the reaction catalyzed by glutathione synthetase.

That is, in the method, step b) may include a step of synthesizing glutathione from glutamate, cysteine and glycine by bifunctional glutathione synthetase while converting adenosine triphosphate generated in step a) into adenosine diphosphate and an inorganic phosphate (see overall reaction B of FIG 1b).

In the present invention, enzyme activity is used to express the relative amount of photosynthetic membrane vesicles and each enzyme. As used herein, the term "enzyme activity" (hereinafter, activity) refers to the amount of product that may be produced per unit time (µmole product/min) by a certain amount of enzyme, and reflects the amount of enzyme that is actually active. The term "relative activity" refers to the ratio of corresponding enzymes or chromatophore membrane vesicles when the actual activity ratio between chromatophore membrane vesicles and enzymes is expressed as a simple integer ratio. In overall reaction A, the relative activity ratio of γ-glutamylcysteine synthetase to glutathione synthetase is preferably 1:1 to 100:1, more preferably 4:1 to 20:1, most preferably 8:1 to 16:1, without being limited thereto. In addition, the relative activity ratio of photosynthetic membrane vesicles to γ-glutamylcysteine synthetase to glutathione synthetase is preferably 1:12:1 to 100:12:1, more preferably 1:12:1 to 50:12:1, most preferably 1:12:1 to 25:12:1, without being limited thereto. In addition, the relative activity ratio of photosynthetic membrane vesicles to bifunctional glutathione synthetase is preferably 1:1 to 1000:1, more preferably 10:1 to 500:1, most preferably 40:1 to 200:1, without being limited thereto. Although production of glutathione is still possible even upon deviating from these relative activity ratios, it is more efficient to follow the ratio in consideration of the total yield of glutathione and production costs.

According to a preferred embodiment of the present invention, the overall reaction A or overall reaction B is performed under anaerobic conditions, which may maximize the activity of photosynthetic membrane vesicles and prevent oxidation of the glutathione product.

Yet another aspect of the present invention provides a composition for producing glutathione, the composition including i) photosynthetic membrane vesicles; and ii) enzymes that catalyze glutathione synthesis, wherein the enzymes are selected from the group consisting of γ-glutamylcysteine synthetase (GSH-I), glutathione synthetase (GSH-II) and bifunctional glutathione synthetase (bifunctional γ-glutamylcysteine synthetase/glutathione synthetase, GshF).

The substance of the present invention may be produced in the form of a composition, and the composition of the present invention may be distributed in suitable containers (e.g., glass bottles, plastic containers, etc.). Thus, the composition of the present invention may be utilized in the production of glutathione. A person who intends to produce glutathione may continuously produce glutathione by irradiating the composition of the present invention containing the photosynthetic membrane vesicles and enzymes that catalyze glutathione synthesis with light.

Yet another aspect of the present invention provides a system for continuously producing glutathione, the system including i) photosynthetic membrane vesicles as a means for supplying adenosine triphosphate; and ii) enzymes that catalyze glutathione synthesis, wherein the enzymes are selected from the group consisting of γ-glutamylcysteine synthetase (GSH-I), glutathione synthetase (GSH-II) and bifunctional glutathione synthetase (bifunctional γ-glutamylcysteine synthetase/glutathione synthetase, GshF), as a means for catalyzing glutathione synthesis.

As used herein, the term "system for continuously producing glutathione" refers to a system in which additional input is not necessarily required other than initial input of adenosine triphosphate or initial input of adenosine diphosphate and an inorganic phosphate and a system that can continuously produce glutathione even when only glutamate, cysteine and glycine are added, and the system includes reactors, kits, devices, equipment, and the like.

Yet another aspect of the present invention provides a method of continuously producing glutathione, the method including a step of adding glutamate, cysteine and glycine as substrates for producing glutathione to the system of the present invention.

Advantageous Effects

The features and advantages of the present invention are summarized as follows:
(i) The present invention provides a method of producing glutathione using photosynthetic membrane vesicles, γ-glutamylcysteine synthetase and glutathione synthetase.
(ii) In addition, the present invention provides a method of producing glutathione using photosynthetic membrane vesicles and bifunctional glutathione synthetase.
(iii) According to the present invention, photosynthetic membrane vesicles are used as a means for supplying adenosine triphosphate which is consumed when γ-glutamylcysteine synthetase, glutathione synthetase or bifunctional glutathione synthetase catalyzes the synthesis of glutathione. That is, since adenosine triphosphate is continuously supplied under light conditions, it is not necessary to additionally supply adenosine triphosphate. Thus, the cost can be reduced.

MODES OF THE INVENTION

Hereinafter, the present invention is described in more detail with reference to the following examples. These examples are only intended to explain the present invention more specifically, and it will be apparent to those skilled in the art that the scope of the present invention is not limited by these examples.

EXAMPLES

Example 1

Isolation of Chromatophore Membrane Vesicles

Chromatophore membrane vesicles are isolated using the method described in Korean Patent Application No. 10-2014-0151907. *Rhodobacter sphearoides* (*Rhodobacter sphearoides* 2.4.1, ATCC BAA-808, Cohen-Bazire et al. 1956. J. Cell. Comp. Physiol. 49: 25-68), a type of purple non-sulfur bacteria, was used to isolate chromatophore membrane vesicles. The strain was cultured in Sistrom's minimal medium (Sistrom. 1962. J. Gen. Microbiol. 28: 607-616, Table 1). The culture method is as follows. First, a test tube containing 5 ml of the medium was inoculated with the strain, and was subjected to shaking culture at 30° C. and 250 rpm. When culture absorbance at 660 nm was about 2.0, the medium was subcultured in an 18-ml screw cap test tube to an initial absorbance of 0.05, and then the screw cap test tube was filled with a fresh medium and sealed to block the exposure to oxygen. Culture was performed under photosynthesis conditions. Specifically, the culture was performed for 18 hours in an incubator, wherein culture conditions were set as follows: temperature is maintained at 30° C. and light is irradiated by an incandescent lamp at a luminous intensity of 15 Watts/m$^2$. After culture, 8 ml of the strain cultured in the 18 ml screw cap test tube was added to a 260 ml transparent bottle, and the remaining volume of the transparent bottle was filled with a fresh medium and sealed. The culture medium was subjected to anaerobic culture, as described above, at a temperature of 30° C. and at a luminous intensity of 15 Watts/m$^2$ for 18 hours. Thereafter, the process of isolating chromatophore membranes was carried out in an anaerobic chamber (anaerobic chamber, model 10, Coy laboratory product). The gas composition in the anaerobic chamber is 90% nitrogen, 5% carbon dioxide and 5% hydrogen. The *Rhodobacter sphearoides* strain cultured in the 260 ml transparent bottle was subjected to centrifugation at 7,000 g and 4° C. for 10 minutes, and then a supernatant was discarded and a cell pellet was obtained. The cell pellet was resuspended in 4 ml of a phosphate buffer (10 mM Na$_2$HPO$_4$, 2 mM KH$_2$PO$_4$, pH 7.6), and a protease inhibitor mixture (protease inhibitor cocktail, Roche) was added thereto according to the manufacturer's instructions. In subsequent procedure, all samples were kept on ice. Next, cell lysis was performed using a sonicator (model VCX130, Sonics & Materials) under the following conditions: ultrasonic irradiation for 2 minutes with 100% amplification and then cooling in ice water for 2 minutes, and repeating this process three times. When irradiating ultrasonic waves, the cell pellets were cooled with ice water to prevent overheating. The lysed cells were subjected to centrifugation at 6,000 g and 4° C. for 10 minutes to obtain a supernatant, and then the supernatant was subjected to centrifugation at 200,000 g and 4° C. for 1 hour using an ultracentrifuge (Optima XE-90, Beckman Coulter). After centrifugation, a supernatant was removed, and a pellet containing chromatophore membrane vesicles was dissolved in 1 ml of a phosphate buffer to perform sucrose-density gradient centrifugation. A sucrose-density gradient was formed in the order of 8 ml of a 60% (w/v, dissolved in a phosphate buffer) sucrose solution, 1 ml of a 40% sucrose solution and 1 ml of a 20% sucrose solution from the bottom layer of an ultracentrifuge tube with a volume of 13.5 ml. 1 ml of the pellet containing chromatophore membrane vesicles was placed on the top layer, and ultracentrifugation was performed at 200,000 g for 4 hours. A reddish brown layer containing chromatophore membrane vesicles was located between a layer of the 20% sucrose solution and a layer of the 40% sucrose solution. The reddish brown layer was separated, and then diluted by addition of the same volume of a phosphate buffer. In addition, kanamycin was added at a concentration of 100 μg/ml to prevent the growth of common contaminants, and a protease inhibitor mixture was added according to the manufacturer's instructions. The mixture was anaerobically sealed and stored at 4° C.

TABLE 1

Composition of Sistrom's minimal medium for culturing *Rhodobacter sphearoides*

| Additives | Final Concentration |
|---|---|
| $KH_2PO_4$ | 20 mM |
| NaCl | 8.5 mM |
| $(NH_4)_2SO_4$ | 3.78 mM |
| L-Glutamate | 0.67 mM |
| L-Aspartic acid | 0.25 mM |
| Succinic acid | 34 mM |
| Nitrilotriacetic acid | 1.05 mM |
| $MgCl_2 \cdot 6H_2O$ | 1.2 mM |
| $CaCl_2 \cdot 2H_2O$ | 0.23 mM |
| $FeSO_4 \cdot 7H_2O$ | 7 μM |
| $(NH_4)_6Mo_7O_{24}$ | 0.16 μM |
| EDTA | 4.7 μM |
| $ZnSO_4 \cdot 7H_2O$ | 38 μM |
| $MnSO_4 \cdot H_2O$ | 9.1 μM |
| $CuSO_4 \cdot 5H_2O$ | 1.6 μM |
| $Co(NO_3)_2 \cdot 6H_2O$ | 0.85 μM |
| $H_3BO_3$ | 1.8 μM |
| Nicotinic acid | 8.1 μM |
| Thiamine hydrochloride | 1.5 μM |
| Biotin | 41 nM |

Example 2

Preparation of Genes Encoding Enzymes Involved in Glutathione Synthesis

To clone genes encoding γ-glutamylcysteine synthetase and glutathione synthetase of overall reaction A (FIG. 1a), respectively, and a gene encoding bifunctional glutathione synthetase of overall reaction B (FIG. 1b), polymerase chain reaction (PCR) was performed. In the case of γ-glutamylcysteine synthetase, SEQ ID NO. 1 and SEQ ID NO. 2 were used as a forward primer and a reverse primer, respectively. In the case of glutathione synthetase, SEQ ID NO. 3 and SEQ ID NO. 4 were used as a forward primer and a reverse primer, respectively. In both cases, the chromosomal DNA of *Escherichia coli* (*Escherichia coli* str. K-12 substr. MG1655) was used as a PCR template. In the case of bifunctional glutathione synthetase, SEQ ID NO. 5 and SEQ ID NO. 6 were used as a forward primer and a reverse primer, respectively, and the chromosomal DNA of *Streptococcus agalactiae* (*Streptococcus agalactiae* str. 2603V/R, ATCC BAA-611) was used as a PCR template. The recognition sequences of a restriction enzyme, Bsa I, and additional sequences recommended by IBA Co. were inserted at both ends of the gene fragments amplified by PCR, and the resulting sequences were ligated to expression vectors, pASK-IBA7plus (in the case of γ-glutamylcysteine synthetase and bifunctional glutathione synthetase) and pASK-IBA3plus (in the case of glutathione synthetase), provided by IBA Co. As a result, gene constructs encoding γ-glutamylcysteine synthetase and bifunctional glutathione synthetase, respectively, in which a strep-tag was attached at the N-terminal, and a gene construct encoding glutathione synthetase, in which a strep-tag was attached to the C-terminal, were obtained.

TABLE 2

Primers for amplifying gene encoding γ-glutamylcysteine synthetase

| SEQ ID NO. | Direction | Sequences |
|---|---|---|
| 1 | gshA-F | 5'-AAAAAAGGTCTCTGCGCTTGATCCCGGACGTATCACA-3' |
| 2 | gshA-R | 5'-AAAAAAGGTCTCTTATCATCAGGCGTGTTTTTCCAGCC-3' |

TABLE 3

Primers for amplifying gene encoding glutathione synthetase

| SEQ ID NO. | Direction | Sequences |
|---|---|---|
| 3 | gshB-F | 5'-AAAAAAGGTCTCTAATGATCAAGCTCGGCATCGT-3' |
| 4 | gshB-R | 5'-AAAAAAGTCTCTGCGCTCTGCTGCTGTAAACGTGCTT-3' |

TABLE 4

Primers for amplifying gene encoding bifunctional glutathione synthetase

| SEQ ID NO. | Direction | Sequences |
|---|---|---|
| 5 | gshF-F | 5'-AAAAAAGGTCTCAGCGCATG<u>ATTATCGATCG</u><u>ACTGTTAC</u>-3' |
| 6 | gshF-R | 5'-AAAAAAGGTCTCGTATCATTATAATTCTGGGAACAGTTTAG-3' |

Example 3

Purification of Enzymes That Catalyze Glutathione Synthesis Reaction

Figure 2:
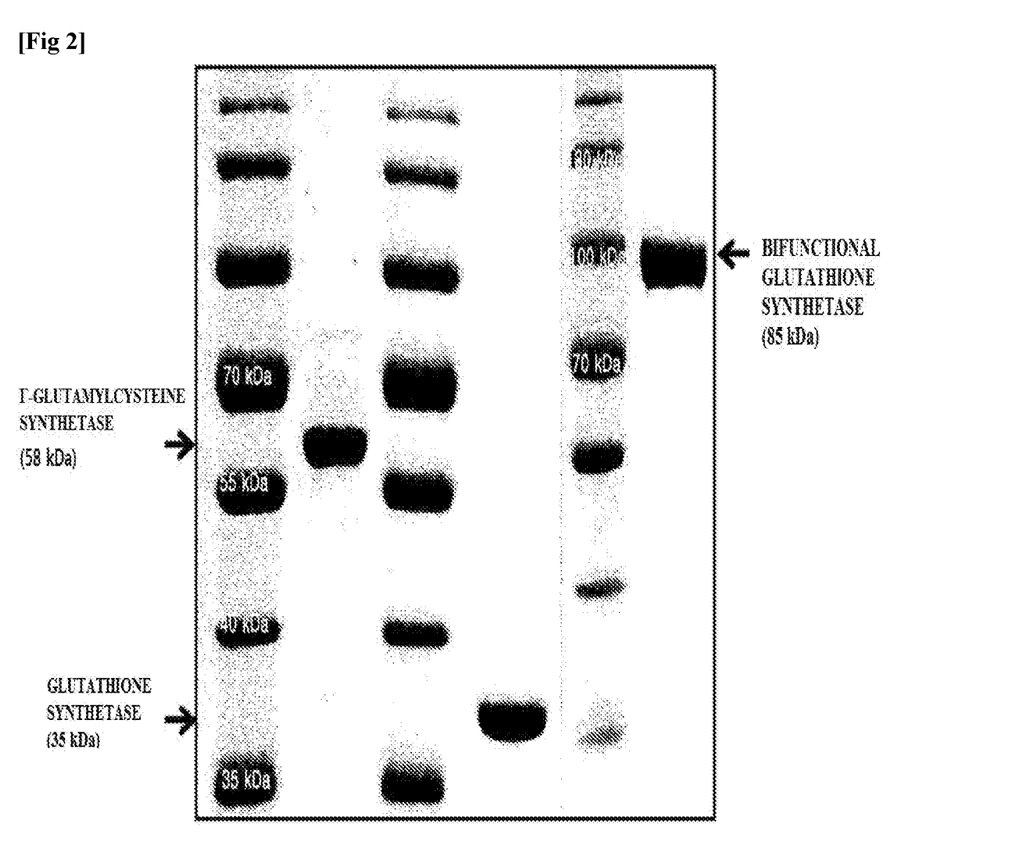
FIG. 2 is an image showing the result of sodium dodecyl sulfate-polyacrylamide gel electrophoresis (SDS-PAGE) performed on purified proteins of the present invention. Each band shown on the image represents purified γ-glutamylcysteine synthetase, glutathione synthetase or bifunctional glutathione synthetase.

*Escherichia coli* strains BL21 (DE3) were transformed with the expression vectors prepared in Example 2, and transformed strains overexpressing γ-glutamylcysteine synthetase, glutathione synthetase and bifunctional glutathione synthetase, respectively, were obtained. The same method was used for purifying these enzymes. First, 5 ml of LB (Luria-Bertani) medium containing 50 μg/ml ampicillin was added to a test tube, and the transformed strain was inoculated in the test tube, followed by shaking culture at 250 rpm and 37° C. for 12 hours. The cells, then, were inoculated into a 1 L flask filled with 500 ml LB medium containing 50 μg/ml ampicillin. At the time of inoculation, an initial absorbance at 600 nm was adjusted to 0.05, and then shaking culture was performed at 250 rpm and 37° C. until absorbance reached 0.4. Anhydrotetracycline was added to the culture at a concentration of 0.2 μg/ml and shaking culture was further continued at 250 rpm and 30° C. for about 12 hours. After culture, cells were centrifuged at 4,000 g for 10 minutes, and a cell pellet was obtained, followed by suspension in 10 ml of buffer W (100 mM Tris-HCl, pH 8.0, 150 mM NaCl, 1 mM EDTA). A protease inhibitor mixture (Roche) was added thereto in an amount recommended by the manufacturer, and the cell pellet was lysed using a sonicator (Branson sonifier 250). Sonication was performed on the suspended cell pellet for 5 minutes at the intensity of output 3, followed by cooling in ice water for 5 minutes. This process was repeated three times. After cell lysis, centrifugation was performed at 6,000 g for 10 minutes to separate a supernatant containing water-soluble enzymes, and the enzymes were purified using strep-tag affinity chromatography. The strep-tag affinity chromatography was performed according to the manufacturer (IBA)'s recommended method. The purified enzymes were verified by 10% SDS polyacrylamide gel electrophoresis (FIG. 2). The expected molecular weights were about 58 kDa for γ-glutamylcysteine synthetase (Watanabe et al. 1986. Nucleic Acids Res. 14: 4393), about 35 kDa for glutathione synthetase (Gushima et al. 1984. Nucleic Acids Res. 12: 9299), and about 85 kDa for bifunctional glutathione synthetase (Janowiak and Griffith. 2005. J. Biol. Chem. 280: 11829-11839).

Example 4

Measurement of Adenosine Triphosphate Production Activity of Chromatophore Membrane Vesicles Under Light Irradiation The quantification and activity measurement of chromatophore membrane vesicles were carried out according to the method described in Korean Patent Application No. 10-2014-0151907. Chromatophore membrane vesicles were quantified using a bacteriochlorophyll α (bch α) concentration. When measuring adenosine triphosphate (ATP) production activity, chromatophore membrane vesicles were used at a concentration of 0.25-0.5 μg bch a/ml. An appropriate amount of chromatophore membrane vesicles was added to a buffer containing 10 mM sodium phosphate ($Na_2HPO_4$), 2 mM potassium phosphate ($KH_2PO_4$), 10 mM magnesium chloride ($MgCl_2$), and 0.4 mM adenosine diphosphate, and the mixture was allowed to react under anaerobic conditions in which a temperature was maintained at 30° C. and light having a luminous intensity of 15 Watts/m$^2$ was irradiated by incandescent lamp. The amount of adenosine triphosphate produced over time was measured by an adenosine triphosphate detection kit (Sigma-Aldrich). The activity of chromatophore membrane vesicles was expressed as the amount of adenosine triphosphate produced per unit time (nmole ATP/min).

Example 5

Figure 3:
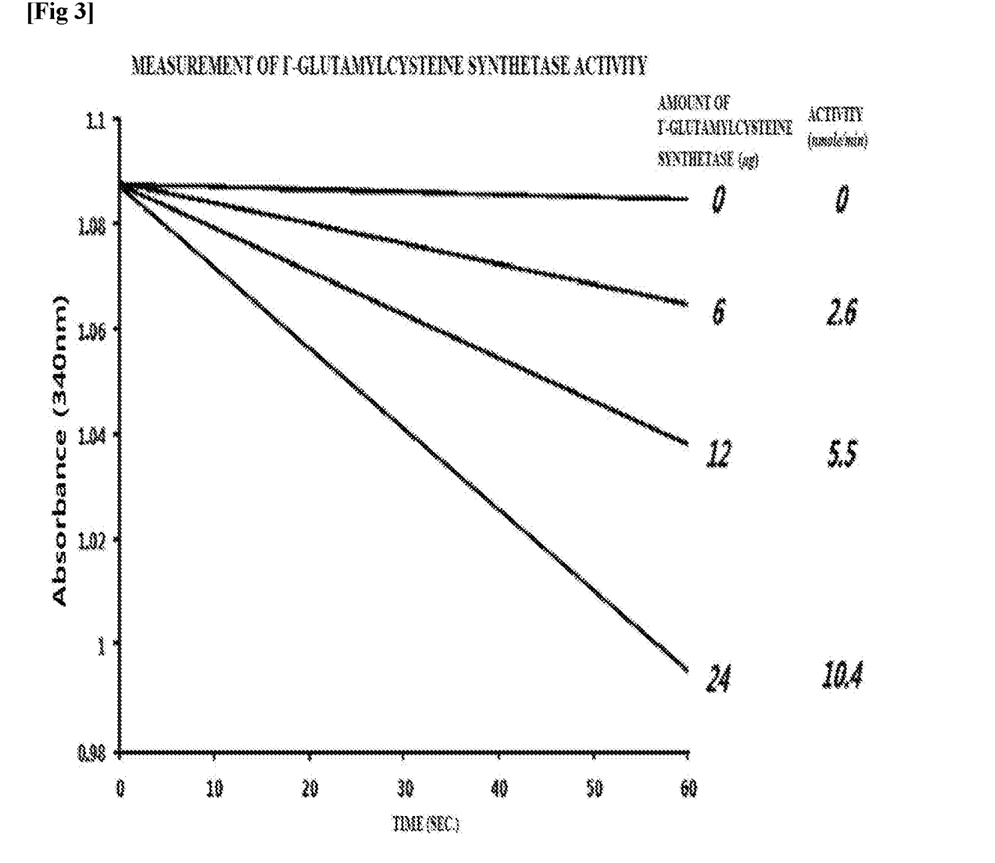
FIG. 3 is a graph showing the activity of γ-glutamylcysteine synthetase measured using a method of detecting adenosine diphosphate formation.
Figure 4:
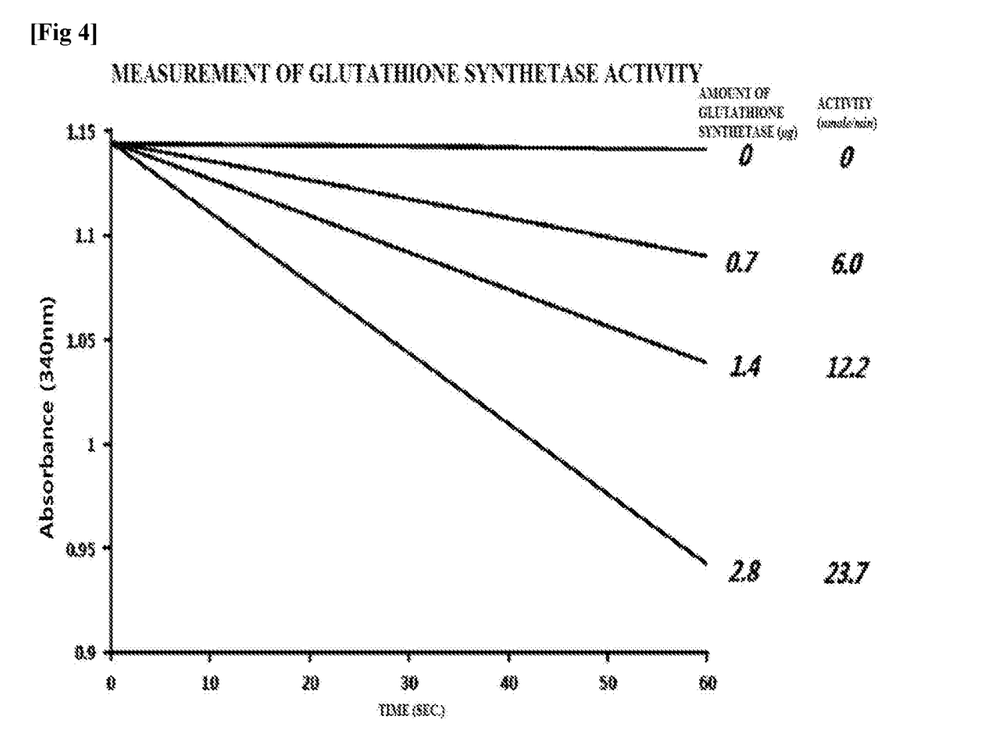
FIG. 4 is a graph showing the activity of glutathione synthetase measured using a method of detecting adenosine diphosphate formation.

Measurement of Enzyme Activity of γ-Glutamylcysteine Synthetase and Glutathione Synthetase To measure enzyme activity of γ-glutamylcysteine synthetase and glutathione synthetase purified in Example 3, a method of measuring adenosine diphosphate formation (Seelig and Meister. 1985. Methods in Enzymol. 113: 379-390) was used. A reaction buffer containing 0.1 mM Tris (Tris-Cl, pH 7.6), 10 mM magnesium chloride ($MgCl_2$), 0.8 mM adenosine triphosphate (ATP), 2 mM phosphoenolpyruvate, 0.2 mM reduced nicotinamide adenine dinucleotide (NADH), 14.3 Unit/ml pyruvate kinase, and 14.3 Unit/ml lactic dehydrogenase was used for activity measurement. When measuring the activity of γ-glutamylcysteine synthetase, 10 mM L-glutamate and 10 mM L-cysteine were added to the reaction buffer. When measuring the activity of glutathione synthetase, 10 mM glycine and 1 mM γ-glutamylcysteine were added to the reaction buffer. The reaction temperature was 30° C. When γ-glutamylcysteine synthetase and glutathione synthetase perform enzymatic reactions, adenosine diphosphate is produced, and at the same time, an amount of reduced nicotinamide adenine dinucleotide (NADH) equivalent to that of the adenosine diphosphate is converted into the oxidized form (NAD$^+$). Since NADH absorbs light at 340 nm and NAD$^+$ does not absorb light at 340 nm, the activity of the two enzymes can be determined by measuring the decrease in absorbance at 340 nm over time. FIG. 3 is a graph showing the result of measurement of γ-glutamylcysteine synthetase activity, and FIG. 4 is a graph showing the result of measurement of glutathione synthetase activity. When the enzyme activity was calculated, the change in the concentration of NADH was determined using a molar extinction coefficient (6,220 $M^{-1}cm^{-1}$) at 340 nm, and it was assumed that one equivalent of the product of each enzyme was produced when one equivalent of NADH was consumed. The calculated amount of product per unit time (nmole product/min) is referred to as enzyme activity.

Example 6

Figure 5:
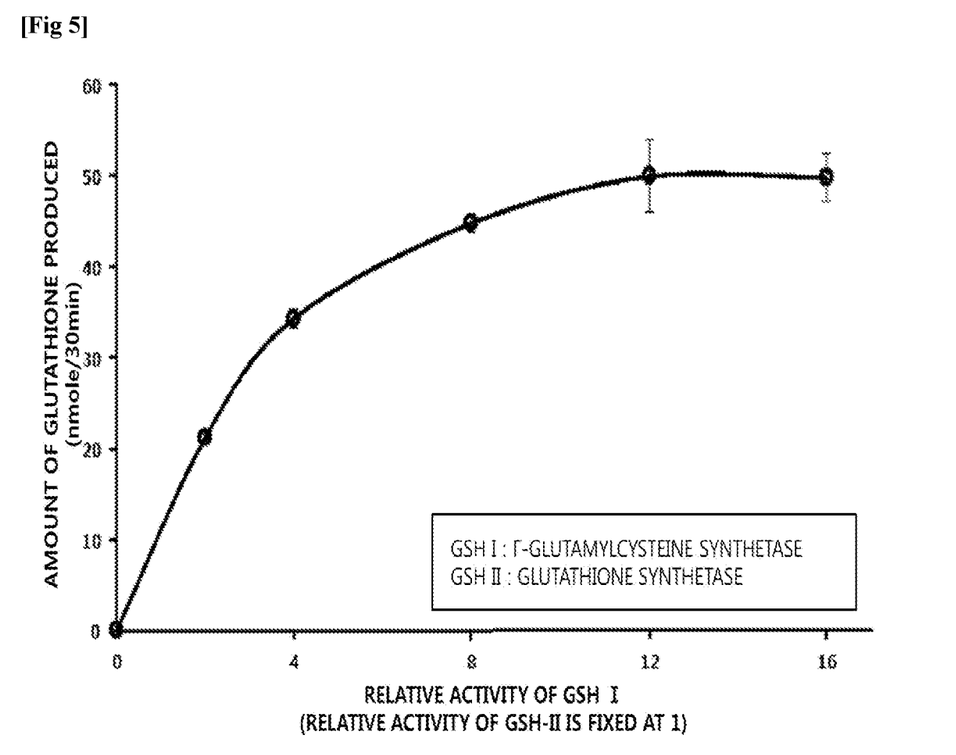
FIG. 5 is a graph showing the amount of glutathione produced depending on the relative activity of γ-glutamylcysteine synthetase while the relative activity of glutathione synthetase is fixed at 1.

Confirmation of Glutathione Production by γ-Glutamylcysteine Synthetase and Glutathione Synthetase In this example, it was confirmed that glutathione was produced from L-glutamate, L-cysteine, glycine and adenosine triphosphate by γ-glutamylcysteine synthetase and glutathione synthetase. A reaction buffer containing 10 mM sodium phosphate ($Na_2HPO_4$), 2 mM potassium phosphate ($KH_2PO_4$), 10 mM magnesium chloride ($MgCl_2$), 0.8 mM adenosine triphosphate (ATP), 10 mM L-glutamate, 10 mM L-cysteine, and 10 mM glycine was used. To prevent oxidation of the resulting glutathione, the reaction was performed at 30° C. under anaerobic conditions. A glutathione detection kit (GSH-Glo™ Glutathione Assay, Promega) was used to detect glutathione. The activity of each enzyme was measured using the method described in Example 5, and relative activity of each enzyme was adjusted based on the measured activity. FIG. 5 is a graph showing the amount of glutathione produced depending on the relative activity of γ-glutamylcysteine synthetase. At this time, the relative activity of glutathione synthetase was fixed at 1, and the relative activity of γ-glutamylcysteine synthetase was varied based on the relative activity of glutathione synthetase. As a result, it was confirmed that glutathione was produced by the two enzymes, and the minimum activity ratio (i.e., GSH-I:GSH-II of FIG. 5) between the two enzymes with the highest glutathione production was about 12:1. Thus, in the following example, the ratio of γ-glutamylcysteine synthetase to glutathione synthetase was used at 12:1.

Example 7

Figure 6:
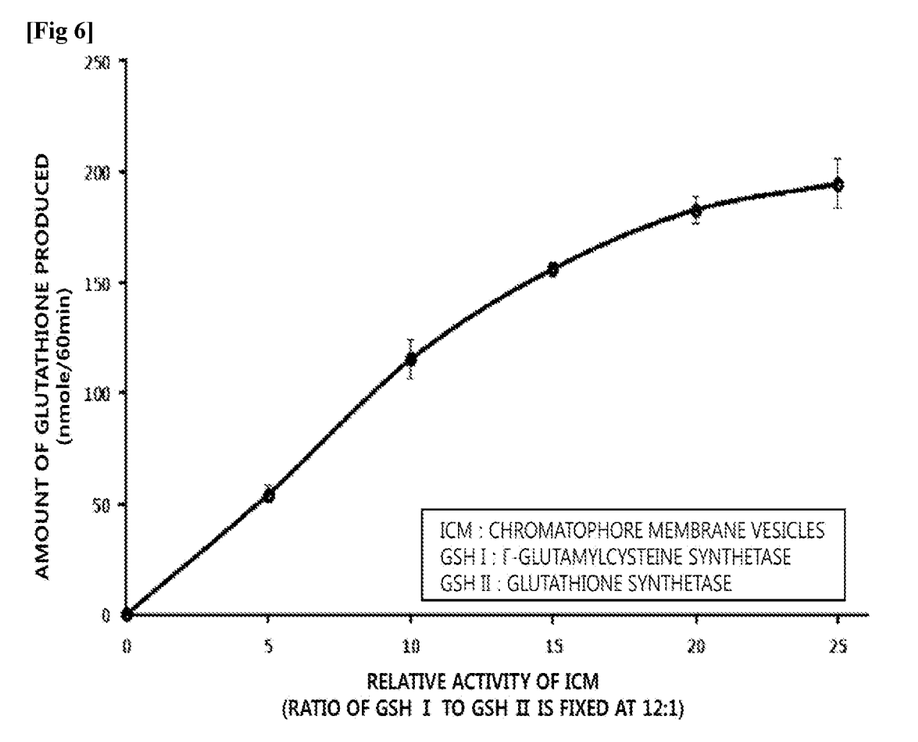
FIG. 6 is a graph showing the amount of glutathione produced depending on the relative activity of chromatophore membrane vesicles while the relative activity of γ-glutamylcysteine synthetase to the relative activity of glutathione synthetase was fixed at 12:1.

Confirmation of Glutathione Production by Chromatophore Membrane Vesicles, γ-Glutamylcysteine Synthetase and Glutathione Synthetase Under Light Conditions In this example, it was confirmed that glutathione was produced by chromatophore membrane vesicles, γ-glutamylcysteine synthetase, and glutathione synthetase in the conditions in which adenosine triphosphate (ATP) was not supplied but light was irradiated. A reaction buffer containing 10 mM sodium phosphate ($Na_2HPO_4$), 2 mM potassium phosphate ($KH_2PO_4$), 10 mM magnesium chloride ($MgCl_2$), 0.4 mM adenosine diphosphate (ADP), 10 mM L-glutamate, 10 mM L-cysteine, and 10 mM glycine was used, and the reaction was performed at 30° C. under anaerobic conditions. An incandescent lamp with a luminous intensity of 15 Watts/$m^2$ was used as a light source. FIG. 6 is a graph showing the amount of glutathione produced depending on the relative activity of chromatophore membrane vesicles. At this time, the relative activity of γ-glutamylcysteine synthetase to the relative activity of glutathione synthetase was fixed at 12:1. As a result, it was confirmed that the amount of glutathione produced (or the rate of glutathione produced) was proportional to the amount of chromatophore membrane vesicles. In addition, when the relative activity of chromatophore membrane vesicles was 25 or more, the amount of glutathione produced was close to maximum.

Example 8

Figure 7:
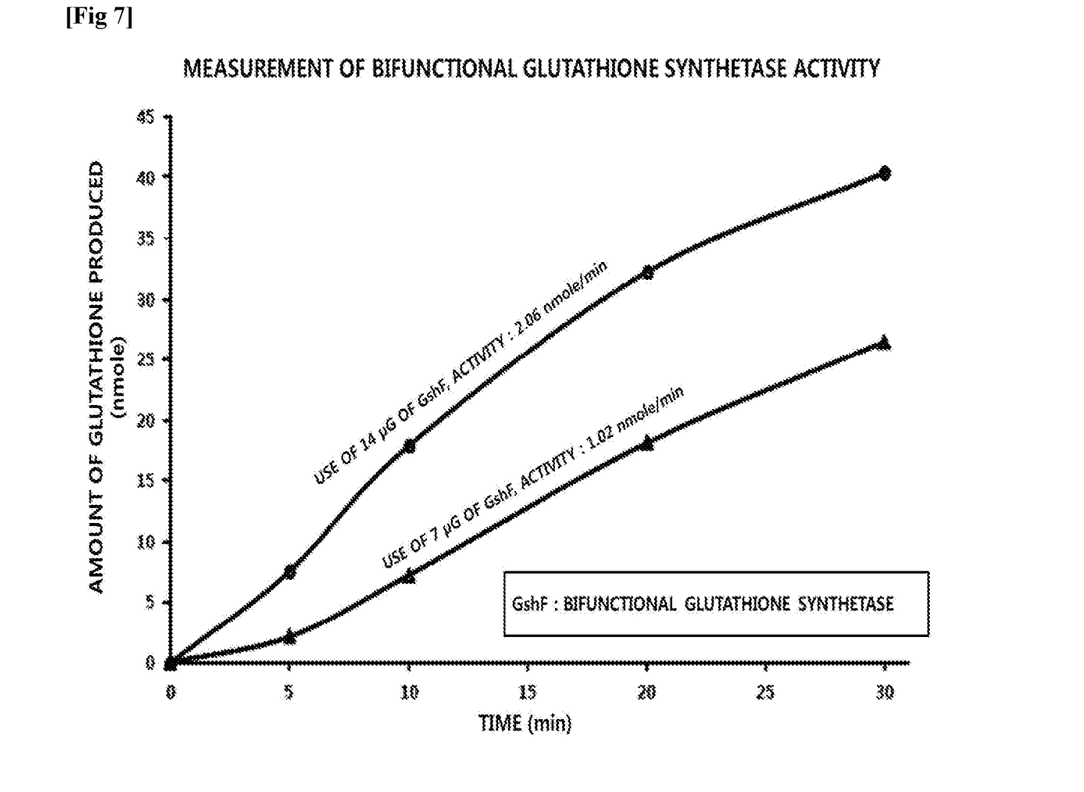
FIG. 7 is a graph showing the activity of bifunctional glutathione synthetase for producing glutathione in a reaction solution containing L-glutamate, L-cysteine, glycine and adenosine triphosphate.

Measurement of Activity of Bifunctional Glutathione Synthetase on Glutathione Production In this example, it was confirmed that glutathione was produced by bifunctional glutathione synthetase in a reaction solution containing L-glutamate, L-cysteine, glycine, and adenosine triphosphate. The composition of the reaction solution was 10 mM sodium phosphate ($Na_2HPO_4$), 2 mM potassium phosphate ($KH_2PO_4$), 10 mM magnesium chloride ($MgCl_2$), 100 mM L-glutamate, 10 mM L-cysteine, 25 mM glycine, and 0.8 mM adenosine triphosphate (ATP). The reaction was performed at 30° C. FIG. 7 is a graph showing the activity (nmole glutathione/min) of bifunctional glutathione synthetase for producing glutathione, wherein the activity was determined by measuring the amount of glutathione produced over time in each reaction solution containing a different amount of bifunctional glutathione synthetase. Since a lag phase was present at an early stage of the reaction catalyzed by bifunctional glutathione synthetase, the activity was calculated based on the reaction rate of the linear region.

Example 9

Figure 8:
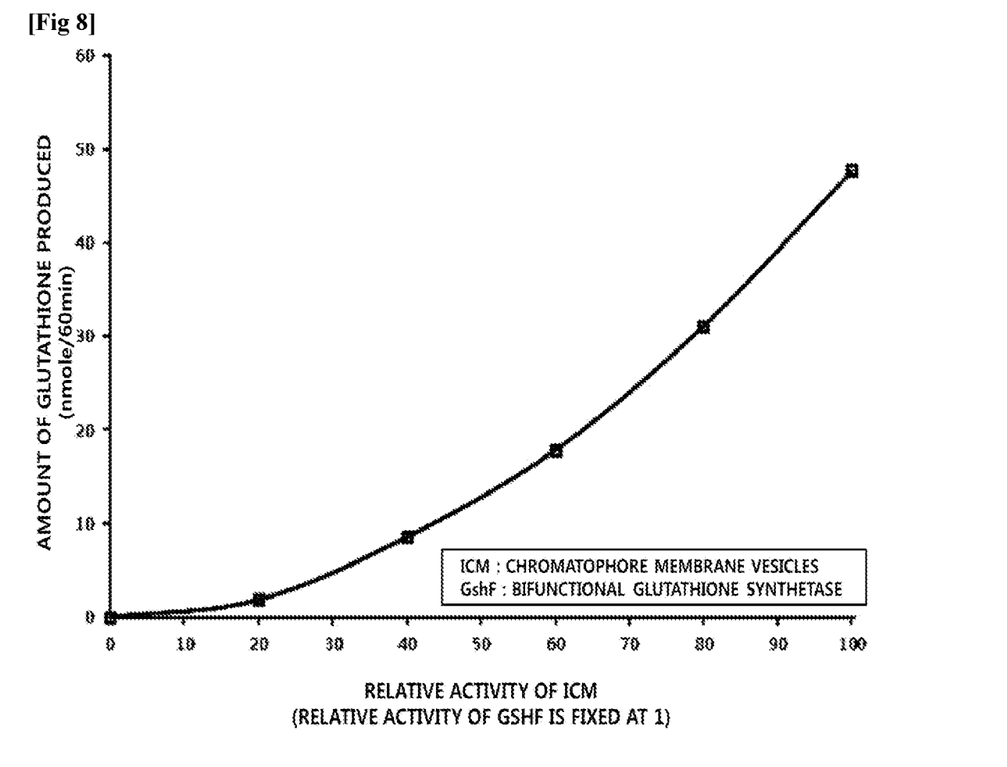
FIG. 8 is a graph showing the amount of glutathione produced depending on the relative activity of chromatophore membrane vesicles while the relative activity of bifunctional glutathione synthetase is fixed at 1.

Confirmation of Glutathione Production by Chromatophore Membrane Vesicles and Bifunctional Glutathione Synthetase Under Light Conditions In this example, it was confirmed that glutathione was produced from L-glutamate, L-cysteine, and glycine when chromatophore membrane vesicles and bifunctional glutathione synthetase were used together under conditions in which adenosine diphosphate was added instead of adenosine triphosphate and light was irradiated. 0.4 mM adenosine diphosphate was added in place of 0.8 mM adenosine triphosphate in the reaction solution of Example 8. The reaction was performed under anaerobic conditions in which temperature is maintained at 30° C. and light was irradiated by an incandescent lamp with a luminous intensity of 15 Watts/$m^2$. FIG. 8 is a graph showing the amount of glutathione produced depending on the relative activity of chromatophore membrane vesicles while the relative activity of bifunctional glutathione synthetase was fixed at 1. It was confirmed that the amount of glutathione produced was proportional to the amount of chromatophore membrane vesicles.

The present invention has been described in detail with reference to preferred embodiments. It will be apparent to those skilled in the art that the preferred embodiments are only illustrative and that the scope of the present invention is not limited thereto. Accordingly, the actual scope of the present invention will be defined by the appended claims and equivalents thereof.

---

The invention claimed is:

1. A method of producing glutathione, comprising:
a) a step of generating adenosine triphosphate (ATP) from adenosine diphosphate (ADP) and an inorganic phosphate by irradiating isolated photosynthetic membrane vesicles with light;
b) a step of synthesizing γ-glutamylcysteine from glutamate and cysteine by γ-glutamylcysteine synthetase while converting adenosine triphosphate generated in step a) into adenosine diphosphate and an inorganic phosphate; and
c) a step of synthesizing glutathione from the synthesized γ-glutamylcysteine and glycine by glutathione synthetase while converting adenosine triphosphate generated in step a) into adenosine diphosphate and an inorganic phosphate,
wherein the photosynthetic membrane vesicles are chromatophore membrane vesicles isolated from purple non-sulfur bacteria, wherein step b) further comprises adding a substrate selected from a group consisting of glutamate, cysteine, or both, and step c) further comprises adding glycine,
wherein a relative activity ratio of the isolated photosynthetic membrane vesicles to γ-glutamylcysteine synthetase to glutathione synthetase is within a range of from 25:12:1 to 50:12:1, and
wherein the steps are carried out under the anaerobic conditions.

2. The method according to claim 1, further comprising d) a step of reusing ADP and an inorganic phosphate forming in step b) to generate ATP in photosynthetic membrane vesicles.

* * * * *

SEQUENCE LISTING

```
<160> NUMBER OF SEQ ID NOS: 6

<210> SEQ ID NO 1
<211> LENGTH: 37
<212> TYPE: DNA
<213> ORGANISM: Artificial Sequence
<220> FEATURE:
<223> OTHER INFORMATION: gamma-glutamylcysteine synthetase forward
      primer (gshA-F)

<400> SEQUENCE: 1
aaaaaaggtc tctgcgcttg atcccggacg tatcaca                                37

<210> SEQ ID NO 2
<211> LENGTH: 38
<212> TYPE: DNA
<213> ORGANISM: Artificial Sequence
<220> FEATURE:
<223> OTHER INFORMATION: gamma-glutamylcysteine synthetase reverse
      primer (gshA-R)
```

```
<400> SEQUENCE: 2
aaaaaaggtc tcttatcatc aggcgtgttt ttccagcc                             38

<210> SEQ ID NO 3
<211> LENGTH: 34
<212> TYPE: DNA
<213> ORGANISM: Artificial Sequence
<220> FEATURE:
<223> OTHER INFORMATION: glutathione synthetase forward primer (gshB-F)

<400> SEQUENCE: 3
aaaaaaggtc tctaatgatc aagctcggca tcgt                                 34

<210> SEQ ID NO 4
<211> LENGTH: 38
<212> TYPE: DNA
<213> ORGANISM: glutathione synthetase reverse primer (gshB-R)
<220> FEATURE:
<223> OTHER INFORMATION: Laboratory-synthesized seqeunce.

<400> SEQUENCE: 4
aaaaaaggtc tctgcgctct gctgctgtaa acgtgctt                             38

<210> SEQ ID NO 5
<211> LENGTH: 39
<212> TYPE: DNA
<213> ORGANISM: Artificial Sequence
<220> FEATURE:
<223> OTHER INFORMATION: bifunctional gamma-glutamylcysteine
      synthetase/glutathione synthetase forward primer (gshF-F)

<400> SEQUENCE: 5
aaaaaaggtc tcagcgcatg attatcgatc gactgttac                            39

<210> SEQ ID NO 6
<211> LENGTH: 41
<212> TYPE: DNA
<213> ORGANISM: rtificial Sequence
<220> FEATURE:
<223> OTHER INFORMATION: bifunctional gamma-glutamylcysteine
      synthetase/glutathione synthetase reverse primer (gshF-R)

<400> SEQUENCE: 6
aaaaaaggtc tcgtatcatt ataattctgg gaacagttta g                         41
```